United States Patent
Inoue et al.

(10) Patent No.: US 10,138,400 B2
(45) Date of Patent: Nov. 27, 2018

(54) HOT MELT ADHESIVE

(71) Applicant: HENKEL AG & CO. KGAA, Duesseldorf (DE)

(72) Inventors: Kentarou Inoue, Osaka (JP); Masahiro Moriguchi, Osaka (JP); Naohiro Maeda, Osaka (JP)

(73) Assignee: Henkel AG & Co., KGaA, Duesseldorf (DE)

( * ) Notice: Subject to any disclaimer, the term of this patent is extended or adjusted under 35 U.S.C. 154(b) by 0 days.

(21) Appl. No.: 15/598,426

(22) Filed: May 18, 2017

(65) Prior Publication Data

US 2017/0253778 A1   Sep. 7, 2017

Related U.S. Application Data

(63) Continuation of application No. 14/865,004, filed on Sep. 25, 2015, now Pat. No. 9,765,245, which is a continuation of application No. PCT/JP2014/058318, filed on Mar. 25, 2014.

(30) Foreign Application Priority Data

Mar. 26, 2013   (JP) .................. 2013-064483

(51) Int. Cl.
    C09J 153/02    (2006.01)
    C08K 5/01      (2006.01)
    C09J 145/00    (2006.01)
    A61F 13/15     (2006.01)

(52) U.S. Cl.
    CPC ............ C09J 153/02 (2013.01); C08K 5/01 (2013.01); C09J 145/00 (2013.01); *A61F 13/15* (2013.01)

(58) Field of Classification Search
    CPC .................................................. C09J 153/02
    See application file for complete search history.

(56) References Cited

U.S. PATENT DOCUMENTS

| | | | |
|---|---|---|---|
| 5,948,527 A | 9/1999 | Gerard et al. | |
| 2008/0070053 A1 | 3/2008 | Schmierer | |
| 2008/0153971 A1 | 6/2008 | Salazar | |
| 2011/0263782 A1* | 10/2011 | Dubois | C08L 53/02 524/505 |
| 2013/0030096 A1 | 1/2013 | Lietzau | |
| 2016/0009966 A1 | 1/2016 | Inoue et al. | |
| 2016/0040047 A1 | 2/2016 | Inoue et al. | |

FOREIGN PATENT DOCUMENTS

| | | | | |
|---|---|---|---|---|
| CN | 101331203 A | | 12/2008 | |
| CN | 101547988 A | | 9/2009 | |
| CN | 102264854 A | | 11/2011 | |
| EP | 1564273 A1 | | 8/2005 | |
| EP | 1564275 A1 | | 8/2005 | |
| JP | 6210163 A | | 1/1987 | |
| JP | 2-232049 A | | 9/1990 | |
| JP | 5311138 A | | 11/1993 | |
| JP | H05-311138 | * | 11/1993 | ............ C09J 153/00 |
| JP | 05331355 A | | 12/1993 | |
| JP | 9-291265 A | | 11/1997 | |
| JP | 10-130349 A | | 5/1998 | |
| JP | 2000282006 A | | 10/2000 | |
| JP | 2000309767 A | | 11/2000 | |
| JP | 2004137297 A | | 5/2004 | |
| JP | 2004238548 A | | 8/2004 | |
| JP | 2006008947 A | | 1/2006 | |
| JP | 2007530714 A | | 11/2007 | |
| JP | 2009511713 A | | 3/2009 | |
| JP | 2010506005 A | | 2/2010 | |
| JP | 2012021078 A | | 2/2010 | |
| JP | 2010536957 A | | 12/2010 | |
| WO | 9928405 A1 | | 6/1999 | |
| WO | 03027182 A1 | | 4/2003 | |
| WO | WO2014017380 A1 | | 7/2016 | |

* cited by examiner

*Primary Examiner* — Robert Harlan
(74) *Attorney, Agent, or Firm* — Sun Hee Lehmann

(57) ABSTRACT

Problem to be solved of the present invention is to provide a hot-melt adhesive agent which is capable of applying at low temperature, has an excellent adhesiveness at low temperature, and a disposable product obtained by employing the hot-melt adhesive agent. Means for solving the problem is a hot-melt adhesive agent comprised of a thermoplastic block copolymer (A) which is a copolymer of vinyl class aromatic hydrocarbons and conjugated diene compounds, wherein the thermoplastic block copolymer (A) comprises a radial type styrene block copolymer having a styrene content of 35 to 45% by weight and a diblock content of 50 to 90% by weight, and having a viscosity at 25° C. as a 25% (by weight) toluene solution of not more than 250 mPa·s (A1).

7 Claims, No Drawings

HOT MELT ADHESIVE

FIELD OF THE INVENTION

The present invention relates to a hot-melt adhesive agent, and more particularly to a hot-melt adhesive agent used in the field of disposable products typified by a paper diaper and a napkin.

BACKGROUND OF THE INVENTION

An adhesive agent containing a thermoplastic block copolymer as a main component has been used in disposable products typified by a paper diaper and a napkin and, particularly, a hot-melt adhesive agent based on a styrene class block copolymer has widely been used. For example, a paper diaper is produced by bonding a polyethylene film with other members (for example, a nonwoven fabric, an elastic material such as a natural rubber, a water-absorbing paper, etc.) using a hot-melt adhesive agent. The hot-melt adhesive agent can be applied to various members using various methods and, even when using any method, the hot-melt adhesive agent is melted by heating so as to obtain an appropriate viscosity, and then the molten adhesive agent is applied to various constituent members in a dot, linear, stripe, spiral or sheet form.

It is now required for the paper diaper to improve drapeness thereof, and a study has been made in improving flexibility and drapeness of the paper diaper by more thinning a polyethylene film or the above-mentioned various members such as a nonwoven fabric. Thinning of various members significantly reduces material costs. However, thinning of the polyethylene film may cause a problem that heat resistance deteriorates and application of a high-temperature (not lower than 150° C.) hot-melt adhesive agent leads to melting of the polyethylene film or formation of wrinkles of the polyethylene film. Therefore, adhesive agent manufacturers have made a progress on the development of a low-temperature-applicable hot-melt adhesive agent which is capable of applying at low temperature (not higher than 140° C.).

Taking workability and environmental aspect in the case of application of the hot-melt adhesive agent into account, manufacturers producing a paper diaper and a sanitary good strongly desire lowering of the viscosity of the hot-melt adhesive agent. The hot-melt adhesive agent commonly comprises a base polymer and a plasticizer, and a study has been made in lowering the viscosity of the hot-melt adhesive agent by a method in which the amount of the base polymer is decreased to thereby increase the amount of the plasticizer. However, the production of a paper diaper using a low viscosity hot-melt adhesive agent produced using such method may cause a problem that the balance between an adhesiveness to a polyethylene film which composes members of the paper diaper and a retention force (cohesive force) is deteriorated, and the softening point is excessively lowered.

JP 2004-137297 A discloses a hot-melt adhesive agent including a linear type styrene block copolymer, a tackifier resin and a plasticizer. The hot-melt adhesive agent of the literature has a low viscosity, and suitable for applying at low temperature, however, is not sufficient in adhesiveness at low temperature.

JP H5(1993)-311138 A, JP 2006-8947 A, and JP 2010-536957 W mention hot-melt adhesive agents including a radial type styrene block copolymer. However, the hot-melt adhesive agents of the Patent Literatures JP H5(1993)-311138 A, JP 2006-8947 A, and JP 2010-536957 W have high melt viscosities, and are not suitable for conducting application at low temperature. These are, however, insufficient in any of peel strength at low temperature, retention force or tack, which are the essential adhesive performances required for the hot-melt adhesive agents for use in a disposable product.

SUMMARY OF THE INVENTION

An object of the present invention is to provide a hot-melt adhesive agent which has an excellent adhesiveness at low temperature, and a disposable product obtained by employing the hot-melt adhesive agent.

The present invention provides a hot-melt adhesive agent including a thermoplastic block copolymer (A) which is a copolymer of vinyl class aromatic hydrocarbons and conjugated diene compounds, wherein the thermoplastic block copolymer (A) comprises a radial type styrene block copolymer having a styrene content of 35 to 45% by weight and a diblock content of 50 to 90% by weight, and having a viscosity at 25° C. as 25% (by weight) toluene solution of not more than 250 mPa·s (A1).

In one embodiment, the radial type styrene block copolymer (A1) comprises at least one selected from the group consisting of a three branched type or a four branched type.

In one embodiment, the hot-melt adhesive agent further comprises a tackifier resin (B) and a plasticizer (C).

In one embodiment, the hot-melt adhesive agent has a content of (A) of 15 to 30 parts by weight, based on 100 parts by weight of the total weight of (A) to (C).

In one embodiment, the thermoplastic block copolymer (A) further comprises a linear type styrene block copolymer (A2).

In one embodiment, the plasticizer (C) comprises at least one selected from the group consisting of naphthene oil and paraffin oil.

DETAILED DESCRIPTION OF THE INVENTION

The present invention also provides a disposable product obtained by applying any one of the above hot-melt adhesive agents.

The hot-melt adhesive agent of the present invention is capable of applying at low temperature because of low melt viscosity, and is excellent in adhesiveness at low temperature, and is also excellent in balance between tack and retention force (cohesive force).

The disposable product of the present invention is composed by adhering with the hot-melt adhesive agent the parts such as a polyethylene film and a nonwoven web, and therefore, each of the parts does not peel off even under a low temperature during the winter season.

In the present invention, the "thermoplastic block copolymer (A)" is a copolymer obtained by block copolymerization of vinyl class aromatic hydrocarbons with conjugated diene compounds, and is usually a resin composition including those which include a vinyl class aromatic hydrocarbon block and a conjugated diene compound block.

As used herein, the "vinyl class aromatic hydrocarbon" means an aromatic hydrocarbon compound having a vinyl group, and specific examples thereof include styrene, o-methylstyrene, p-methylstyrene, p-tert-butylstyrene, 1,3-dimethylstyrene, α-methylstyrene, vinylnaphthalene, vinylanthracene, and the like. Particularly, styrene is preferable. These vinyl class aromatic hydrocarbons can be used alone or in combination.

The "conjugated diene compound" means a diolefin compound having at least a pair of conjugated double bonds. Specific examples of the "conjugated diene compound" include 1,3-butadiene, 2-methyl-1,3-butadiene (or isoprene), 2,3-dimethyl-1,3-butadiene, 1,3-pentadiene, and 1,3-hexadiene. Particularly, 1,3-butadiene and 2-methyl-1,3-butadiene are preferable. These conjugated diene compounds can be used alone or in combination.

The thermoplastic block copolymer (A) according to the present invention may be either an unhydrogenated product or a hydrogenated product.

Specific examples of the "unhydrogenated product of the thermoplastic block copolymer (A)" include those in which blocks based on the conjugated diene compound are not hydrogenated. Specific examples of the "hydrogenated product of the thermoplastic block copolymer (A)" include block copolymers in which blocks based on the conjugated diene compound are entirely or partially hydrogenated.

A proportion that the "hydrogenated product of the thermoplastic block copolymer (A)" is hydrogenated can be indicated by a "hydrogenation ratio". The "hydrogenation ratio" of the "hydrogenated product of the thermoplastic block copolymer (A)" refers to a proportion of double bonds converted into saturated hydrocarbon bonds by hydrogenation on the basis of all aliphatic double bonds included in the blocks based on the conjugated diene compound. The "hydrogenation ratio" can be measured by an infrared spectrophotometer, a nuclear magnetic resonance spectrometer, and the like.

Specific examples of the "unhydrogenated product of the thermoplastic block copolymer (A)" include a styrene-isoprene block copolymer (also referred to as "SIS") and a styrene-butadiene block copolymer (also referred to as "SBS"). Specific examples of the "hydrogenated product of the thermoplastic block copolymer (A)" include a hydrogenated styrene-isoprene block copolymer (also referred to as "SEPS") and a hydrogenated styrene-butadiene block copolymer (also referred to as "SEBS").

The thermoplastic block copolymer (A) may be used alone or in combination of the plural classes.

The present invention employs a radial type styrene block copolymer (A1) as a class of the thermoplastic block copolymer (A). The radial type styrene block copolymer is a branched styrene block copolymer having a structure in which a plurality of linear type styrene block copolymers radially project from a coupling agent as the center. The linear type styrene block copolymer is a linear copolymer in which blocks of styrene are bonded with blocks of conjugated diene.

Specific structure of the radial type styrene block copolymer is shown below.

$(S-E)_nY$ (1)

In the formula, n is an integer of not less than 2, S is a styrene block, E is a conjugated diene compound block, and Y is a coupling agent. n is preferably 3 or 4. The polymer in which n is 3 is referred to as a three branched type, while the copolymer in which n is 4 is referred to as a four branched type. When n is 3 or 4, the obtained hot-melt adhesive agent exhibits low melt viscosity and high retention force (cohesive force). The conjugated diene compound is preferably butadiene or isoprene.

The radial type styrene block copolymer (A1) in the present invention is a resin composition, and includes a styrene-conjugated diene block copolymer represented by the formula:

S–E (2)

wherein S and E have the same meanings as defined above, in a given proportion. The styrene-conjugated diene block copolymer of the formula (2) may be sometimes called "diblock".

The coupling agent is a polyfunctional compound which radially bonds a linear type styrene block copolymer. There is no particular limitation on types of the coupling agent.

Examples of the coupling agent include a silane compound such as halogenated silane or alkoxysilane, a tin compound such as halogenated tin, an epoxy compound such as a polycarboxylate ester or epoxydized soybean oil, an acrylic ester such as pentaerythritol tetraacrylate, a divinyl compound such as epoxysilane or divinylbenzene, and the like. Specific examples thereof include trichlorosilane, tribromosilane, tetrachlorosilane, tetrabromosilane, methyltrimethoxysilane, ethyltrimethoxysilane, vinyltrimethoxysilane, vinyltriethoxysilane, tetramethoxysilane, tetraethoxysilane, tetrachlorotin, diethyl adipate, and the like.

In the present invention, the radial type styrene block copolymer (A1) has a styrene content of 35 to 45% by weight, a diblock content of 50 to 90% by weight, and has a viscosity at 25° C. as a 25% (by weight) toluene solution of not more than 250 mPa·s.

The "styrene content" refers to a proportion of a styrene block included in (A1). The styrene content is 35 to 45% by weight, and more preferably 35 to 40% by weight.

The styrene content of (A1) is within the above range, whereby, the hot-melt adhesive agent of the present invention becomes excellent in balance between retention force (cohesive force), tack and adhesiveness at low temperature.

The "diblock content" refers to a proportion of a styrene-conjugated diene compound block copolymer of the formula (2) included in (A1). The diblock content is 50 to 90% by weight, and more preferably 55 to 85% by weight.

The diblock content of (A1) is within the above range, whereby, the hot-melt adhesive agent of the present invention becomes excellent in tack and adhesiveness at low temperature. The diblock content of (A1) of less than 50% by weight may sometimes cause deterioration of either adhesiveness at low temperature or tack of the obtained hot-melt adhesive agent because of excessive content of a branched structure component represented by the formula (1). The diblock content of (A1) of more than 90% by weight may make it difficult to enhance the retention force of the hot-melt adhesive agent even in the case of having a radial structure.

The "viscosity at 25° C. as a 25% (by weight) toluene solution" refers to a viscosity at 25° C. as a solution having a concentration of 25% by weight using toluene as a solvent, and can be measured using various viscometers, for example, a Brookfield BM-type viscometer (spindle No. 27).

The viscosity at 25° C. as a 25% (by weight) toluene solution" of (A1) is not more than 250 mPa·s, and ranges from 100 to 250 mPa·s. Particularly, the viscosity is more preferably 130 to 200 mPa·s.

In the hot-melt adhesive agent of the present invention, the viscosity at 25° C. as a 25% (by weight) toluene solution" of (A1) within the above range may cause significant decrease in melt viscosity, leading to easy application at low temperature.

HJ10, HJ12, HJ13, and HJ15 are commercially available from Asahi Kasei Chemicals Corporation as the radial type styrene block copolymer (A1).

In the present invention, the thermoplastic block copolymer (A) includes a styrene block copolymer different from (A1), and preferably includes a linear type styrene block copolymer (A2). The inclusion of (A2), not only (A1), may enable further improvement in balance between tack, retention force (cohesive force) and adhesiveness at low temperature.

In the present specification, the wording "linear type" means the structures in a linear form. The linear type styrene block copolymer means a styrene block copolymer having a linear form structure.

Commercially available products may be used as the linear type styrene block copolymer. Examples thereof include Asaprene T439 (trade name), Asaprene T436 (trade name) and Asaprene T432 (trade name) manufactured by Asahi Kasei Chemicals Corporation; TR2600 (trade name) manufactured by JSR Corporation; Stereon 857 (trade name) and Stereon 841A (trade name) manufactured by Firestone Corporation; Kraton D1118 (trade name) manufactured by Kraton Polymers, Inc.; Sol T166 (trade name) manufactured by Enichem, Ltd.; Quintac 3433N (trade name) and Quintac 3421 (trade name) manufactured by Zeon Corporation. The commercially available products of the thermoplastic block copolymer (A) may be used alone or in combination.

The thermoplastic block copolymer (A) optionally includes other styrene block copolymers (A3) which do not fall in (A1) or (A2).

Examples of the other styrene block copolymers (A3) include TR2500 (trade name) manufactured by JSR Corporation; Quintac 3450 (trade name) and Quintac 3460 (trade name) manufactured by Zeon Corporation; Sol T6414 (trade name) manufactured by Enichem, Ltd.

The hot-melt adhesive agent of the present invention includes a tackifier resin (B) and a plasticizer (C). The tackifier resin is, not particularly limited as long as, that conventionally employed for a hot-melt adhesive agent, and able to provide the objective hot-melt adhesive agent of the present invention.

Examples of such tackifier resin (B) include a natural rosin, a modified rosin, a hydrogenated rosin, a glycerol ester of a natural rosin, a glycerol ester of a modified rosin, a pentaerythritol ester of a natural rosin, a pentaerythritol ester of a modified rosin, a pentaerythritol ester of a hydrogenated rosin, a copolymer of a natural terpene, a three dimensional polymer of a natural terpene, hydrogenated derivatives of a copolymer of a hydrogenated terpene, a polyterpene resin, hydrogenated derivatives of a phenol class modified terpene resin, an aliphatic petroleum hydrocarbon resin, hydrogenated derivatives of an aliphatic petroleum hydrocarbon resin, an aromatic petroleum hydrocarbon resin, hydrogenated derivatives of an aromatic petroleum hydrocarbon resin, a cyclic aliphatic petroleum hydrocarbon resin, and hydrogenated derivatives of a cyclic aliphatic petroleum hydrocarbon resin. These tackifier resins can be used alone or in combination. It is also possible to use, as the tackifier resin, a liquid type tackifier resin as long as it has a colorless to pale yellow color tone and has substantially no odor, and also has satisfactory thermal stability. When the performances are considered from a comprehensive point of view, a hydrogenated derivative of a resin and the like is preferred as the tackifier resin. An unhydrogenated tackifier resin is optionally employed in combination.

It is possible to use, as the tackifier resin (B), commercially available products. Examples of such commercially available products include ECR179EX (trade name) manufactured by Tonex Co., Ltd.; Maruka Clear H (trade name) manufactured by Maruzen Petrochemical CO, LTD.; Alcon M100 (trade name) manufactured by Arakawa Chemical Industries, Ltd.; I-MARV S100 (trade name) manufactured by IDEMITSU KOSAN CO., LTD.; Clearon K100 (trade name), Clearon K4090 (trade name) and Clearon K4100 manufactured by YASUHARA CHEMICAL CO., LTD.; ECR179EX (trade name) and ECR231C (trade name) manufactured by Tonex Co., Ltd.; Regalite C6100L (trade name) and Regalite C8010 (trade name) manufactured by Eastman Chemical Company; and FTR2140 (trade name) manufactured by Mitsui Chemicals, Inc. Examples of the unhydrogenated tackifier resin include Quinton DX390N (trade name) and Quinton DX395 (trade name) manufactured by Zeon Corporation. These commercially available tackifier resins can be used alone or in combination.

The plasticizer (C) is blended for the purpose of decreasing melt viscosity of the hot-melt adhesive agent, imparting flexibility to the hot-melt adhesive agent, and improving wettability of the hot-melt adhesive agent to an adherend. There is no particular limitation as long as the plasticizer is compatible with the block copolymer and the objective hot-melt adhesive agent of the present invention is obtainable. Examples of the plasticizer (C) include paraffin oil, naphthene oil and aromatic oil. Colorless and odorless naphthene oil is particularly preferable.

It is possible to use, as the plasticizer (C), commercially available products. Examples thereof include White Oil Broom 350 (trade name) manufactured by Kukdong Oil & Chemicals Co., Ltd.; Diana Fresia S32 (trade name), Diana Process Oil PW-90 (trade name) and DN Oil KP-68 (trade name) manufactured by IDEMITSU KOSAN CO., LTD.; Enerper M1930 (trade name) manufactured by BP Chemicals, Inc.; Kaydol (trade name) manufactured by Crompton Corporation; Primol352 (trade name) manufactured by ESSO Corp.; Process Oil NS100 manufactured by IDEMITSU KOSAN CO., LTD.; and KN4010 (trade name) manufactured by PetroChina Company Limited. These plasticizers (C) can be used alone or in combination.

In the hot-melt adhesive agent of the present invention, the content of (A) is 3 to 60 parts by weight, preferably 8 to 45 parts by weight, more preferably 15 to 35 parts by weight, and particularly preferably 10 to 30 parts by weight, based on 100 parts by weight of the total weight of (A) to (C). The content of (A) within the above range may enable the hot-melt adhesive agent to be excellent in adhesiveness at low temperature, tack and retention force, and to be capable of applying at low temperature.

If necessary, the hot-melt adhesive agent according to the present invention optionally further contains various additives. Examples of such various additives include a stabilizer and a fine particle filler.

The "stabilizer" is blended so as to prevent decrease in molecular weight, occurrence of gelation, coloration, odor and the like of the hot-melt adhesive agent due to heat, thereby improving stability of the hot-melt adhesive agent, and there is no particular limitation as long as the objective hot-melt adhesive agent of the present invention is obtainable. Examples of the "stabilizer" include an antioxidant and an ultraviolet absorber.

The "ultraviolet absorber" is used so as to improve light resistance of the hot-melt adhesive agent. The "antioxidant" is used so as to prevent oxidative degradation of the hot-melt adhesive agent. There is no particular limitation on the antioxidant and the ultraviolet absorber, as long as they are commonly used in disposable products and the below-mentioned objective disposable products are obtainable.

Examples of the antioxidant include phenol antioxidants, sulfur antioxidants and phosphorous antioxidants. Examples of the ultraviolet absorber include benzotriazole ultraviolet absorbers and benzophenone ultraviolet absorbers. It is also possible to add lactone stabilizers. These additives can be used alone or in combination.

It is possible to use, as the stabilizer, commercially available products. Examples thereof include SUMILIZER GM (trade name), SUMILIZER TPD (trade name) and SUMILIZER TPS (trade name) manufactured by Sumitomo Chemical Co. Ltd.; IRGANOX 1010 (trade name), IRGANOX HP2225FF (trade name), IRGAFOS 168 (trade name) and IRGANOX 1520 (trade name) manufactured by Ciba Specialty Chemicals Inc.; and JF77 (trade name) manufactured by Johoku Chemical Co., Ltd. These stabilizers can be used alone or in combination.

The hot-melt adhesive agent of the present invention is produced by blending the above components in a given proportion, optionally blending various additives, and melting the mixture with heating, followed by mixing. Specifically, the hot-melt adhesive agent is produced by charging the above components in a melt-mixing vessel equipped with a stirrer, followed by mixing with heating.

The obtained hot-melt adhesive agent preferably has a melt viscosity at 120° C. of not more than 10,000 mPa·s and a melt viscosity at 140° C. of not more than 5,000 mPa·s, and a softening point of not lower than 75° C. The "melt viscosity" refers to a viscosity in molten state of the hot-melt adhesive agent and is measured by a Brookfield RVT-type viscometer (spindle No. 27). The "softening point" refers to a temperature at which the hot-melt adhesive agent becomes soft and starts deforming when the material is heated. It is measured by the Ring and Ball method (the method determined as Japan Adhesive Industry Association Standard JAI-7-1999).

The hot-melt adhesive agent according to the present invention has a melt viscosity at 120° C. of not more than 10,000 mPa·s and a viscosity at 140° C. of not more than 5,000 mPa·s, and therefore, is capable of applying at law temperature (not higher than 140° C.). In addition, when the softening point is not lower than 75° C., the hot-melt adhesive agent can be fed in liquid form or semi-liquid form. The hot-melt adhesive agent is preferred from the environmental point of view because it is able to be stored in a temperature keeping container in liquid form or semi-liquid form, and is able to be fed as it is. That is, generation of waste materials is able to be reduced, and power consumption is able to be saved when the hot-melt adhesive agent is produced.

The hot-melt adhesive agent according to the present invention preferably has a retention force at 40° C. of not less than 10 minutes, more preferably not less than 30 minutes, and particularly preferably not less than 50 minutes on the method for evaluation of retention force mentioned in Examples.

The hot-melt adhesive agent according to the present invention preferably has a peel strength (10° C., 20° C.) of not less than 1,000 gf/inch (8.8 N/2.54 cm), and more preferably 2,000 gf/inch (9.8 N/2.54 cm), measured by the method for evaluation of peel strength mentioned in Examples.

The hot-melt adhesive agent according to the present invention preferably has loop tack of not less than 1,000 gf/inch (9.8 N/2.54 cm), more preferably 1,500 gf/inch (14.7 N/2.54 cm), and particularly preferably not less than 2,000 gf/inch (19.6 N/2.54 cm), measured by the method for evaluation of loop tack mentioned in Examples.

The hot-melt adhesive agent according to the present invention is widely used in paper processing, bookbinding, disposable products, and the like, and is mainly used in disposable products. There is no particular limitation on "disposable products" as long as they are so-called sanitary materials. Specific examples thereof include a paper diaper, a sanitary napkin, a pet sheet, a hospital gown, a surgical white garment, and the like.

The present invention provides, in another aspect, a disposable product obtained by non-contact coating of the above hot-melt adhesive agent at low temperature (not higher than 140° C.). The disposable product is constituted by bonding at least one member selected from the group consisting of a woven fabric, a nonwoven fabric, a rubber, a resin and papers with a polyolefin film using the hot-melt adhesive agent according to the present invention. The polyolefin film is preferably a polyethylene film for the reason of durability, costs and the like.

In the production line for the disposable product, the hot-melt adhesive agent is commonly applied to at least one of various members (for example, nonwoven fabric, etc.) of the disposable product, and a polyolefin film, and then the film is contact-bonded with the members to produce a disposable product. In the case of applying, the hot-melt adhesive agent may be discharged from various ejectors. In the present invention, the "non-contact coating" method refers to a coating method in which a discharger is not brought into contact with a member or a film in the case of applying the hot-melt adhesive agent. Specific examples of the non-contact coating method include a spiral coating method capable of coating in a spiral form, an omega coating or control seam coating method capable of coating in a wavy form, a slot spray coating or curtain spray coating method capable of coating in a plane form, a dot coating method capable of coating in a dot form, and the like.

EXAMPLES

The present invention will be described for the purpose of describing the present invention in more detail and specific manner by way of Examples and Comparative Examples. These are exemplary of the present invention and are not to be considered as limiting.

In Examples, unless otherwise specified, parts by weight and percentages by weight are based on the places where a solvent is not taken into account.

Components used in the present Examples are shown below.

(A) Thermoplastic Block Copolymer
<(A1) Radial Type Styrene Block Copolymer>
(A1-1) Three branched type styrene-butadiene block copolymer (styrene content of 39% by weight, diblock content of 80% by weight, viscosity at 25° C. as 25% (by weight) toluene solution of 165 mPa·s, HJ13 (manufactured by Asahi Kasei Chemicals Corporation))
(A1-2) Three branched type styrene-butadiene block copolymer (styrene content of 38% by weight, diblock content of 80% by weight, viscosity at 25° C. as 25% (by weight) toluene solution of 184 mPa·s, HJ12 (manufactured by Asahi Kasei Chemicals Corporation))
(A1-3) Four branched type styrene-butadiene block copolymer (styrene content of 38% by weight, diblock content of 80% by weight, viscosity at 25° C. as 25% (by weight) toluene solution of 155 mPa·s, HJ15 (manufactured by Asahi Kasei Chemicals Corporation))

(A1-4) Three branched type styrene-butadiene block copolymer (styrene content of 38% by weight, diblock content of 60% by weight, viscosity at 25° C. as 25% (by weight) toluene solution of 177 mPa·s, HJ10 (manufactured by Asahi Kasei Chemicals Corporation))

<(A2) Linear Type Styrene Block Copolymer>

(A2-1) Linear type styrene-butadiene block copolymer (styrene content of 30% by weight, diblock content of 50% by weight, viscosity at 25° C. as 25% (by weight) toluene solution of 3,100 mPa·s, Asaprene T432 (manufactured by Asahi Kasei Chemicals Corporation))

(A2-2) Linear type styrene-isoprene block copolymer (styrene content of 43% by weight, diblock content of 60% by weight, viscosity at 25° C. as 25% (by weight) toluene solution of 170 mPa·s, Asaprene T439 (manufactured by Asahi Kasei Chemicals Corporation))

(A2-3) Linear type styrene-isoprene block copolymer (styrene content of 16% by weight, diblock content of 56% by weight, viscosity at 25° C. as 25% (by weight) toluene solution of 810 mPa·s, Quintac 3433N (manufactured by Zeon Corporation))

<(A3) Other Styrene Block Copolymers>

(A3-1) Three branched type styrene-butadiene block copolymer (styrene content of 35% by weight, diblock content of 40% by weight, viscosity at 25° C. as 25% (by weight) toluene solution of 490 mPa·s, JSR TR2500 (manufactured by JSR Corporation))

(A3-2) Four branched type styrene-butadiene block copolymer (styrene content of 40% by weight, diblock content of 20% by weight, viscosity at 25° C. as 25% (by weight) toluene solution of 400 mPa·s, Sol T6414 (manufactured by Enichem, Ltd.))

(A3-3) 14.2 branched type styrene-butadiene block copolymer (styrene content of 30% by weight, diblock content of 50% by weight, viscosity at 25° C. as 25% (by weight) toluene solution of 600 mPa·s, Soloprene 9618 (manufactured by Dynasol Inc.))

(A3-4) Three branched type styrene-isoprene block copolymer (styrene content of 25% by weight, diblock content of 40% by weight, viscosity at 25° C. as 25% (by weight) toluene solution of 380 mPa·s, Quintack 3460 (manufactured by Zeon Corporation))

(A3-5) Three branched type styrene-isoprene block copolymer (styrene content of 19% by weight, diblock content of 30% by weight, viscosity at 25° C. as 25% (by weight) toluene solution of 550 mPa·s, Quintack 3450 (manufactured by Zeon Corporation))

(B) Tackifier Resin (B1) Hydrogenated tackifier resin (ECR179EX (manufactured by Exxon Mobil Corporation))

(B2) Hydrogenated tackifier resin (Alcon M100 (manufactured by Arakawa Chemical Industries, Ltd.))

(B3) Hydrogenated tackifier resin (I-MARV S100N (manufactured by IDEMITSU KOSAN CO., LTD.))

(B4) Hydrogenated tackifier resin (Regalite C6100L (manufactured by Eastman Chemical Company))

(B5) Unhydrogenated tackifier resin (Quinton DX390N (manufactured by Zeon Corporation))

(B6) Liquid tackifier resin (Maruka Clear H (manufactured by Maruzen Petrochemical CO, LTD.))

(B7) Hydrogenated tackifier resin (Plastolyn 240 (manufactured by Eastman Chemical Company))

(C) Plasticizer (C1) Paraffin oil (Diana Fresis S-32 (manufactured by IDEMITSU KOSAN CO., LTD.))

(C2) Paraffin oil (Daphne Oil KP68 (manufactured by IDEMITSU KOSAN CO., LTD.))

(C3) Naphthene oil (Process Oil NS100 (manufactured by IDEMITSU KOSAN CO., LTD.))

(C4) Naphthene oil (KN4010 (manufactured by PetroChina Company Limited.))

(D) Wax (D1) Maleic anhydride modified polypropylene wax (Rikosen TP MA6252 (manufactured by Clariant (Japan) K.K.))

(E) Antioxidant (E1) Phenol antioxidants (SUMILIZER GM (manufactured by Sumitomo Chemical Co., Ltd.))

(E2) Sulfur antioxidants (SUMILIZER TPD (manufactured by Sumitomo Chemical Co., Ltd.))

(E3) Benzotriazole antioxidants (JF77 (manufactured by Johoku Chemical Co., Ltd.))

Preparation of hot-melt adhesive agents of Examples 1 to 7 and Comparative Examples 1 to 6 are as follows.

The respective components were blended according to the formulations shown in Tables 1 to 4, and then melt-mixed at about 150° C. to prepare hot-melt adhesive agents. In Tables 1 to 4, "St" means a styrene content, "diblock" means a diblock content, and "TV" means a viscosity at 25° C. as a 25% (by weight) toluene solution.

TABLE 1

|     |        |                                                              | Example 1 | Example 2 | Example 3 | Example 4 |
|-----|--------|--------------------------------------------------------------|-----------|-----------|-----------|-----------|
| (A) | (A1-1) | Three branched radial (St: 39%, diblock: 80%, TV: 165 mPa · s) | 28        |           |           |           |
|     | (A1-2) | Three branched radial (St: 38%, diblock: 80%, TV: 184 mPa · s) |           | 27        |           |           |
|     | (A1-3) | Four branched radial (St: 38%, diblock: 80%, TV: 155 mPa · s)  |           |           | 28        |           |
|     | (A1-4) | Three branched radial (St: 38%, diblock: 60%, TV: 177 mPa · s) |           |           |           | 27        |
|     | (A2-1) | Linear (St: 30%, diblock: 50%, TV: 3100 mPa · s)             |           |           |           |           |
|     | (A2-2) | Linear (St: 43%, diblock: 60%, TV: 170 mPa · s)              |           |           |           |           |
|     | (A2-3) | Linear (St: 16%, diblock: 56%, TV: 810 mPa · s)              |           |           |           |           |
|     | (A3-1) | Three branched radial (St: 35%, diblock: 40%, TV: 490 mPa · s) |           |           |           |           |
|     | (A3-2) | Four branched radial (St: 40%, diblock 20%, TV; 400 mPa · s)   |           |           |           |           |
|     | (A3-3) | 14.2 Branched radial (St: 30%, diblock: 50%, TV: 600 mPa · s)  |           |           |           |           |

TABLE 1-continued

|   |   |   | Example 1 | Example 2 | Example 3 | Example 4 |
|---|---|---|---|---|---|---|
|   | (A3-4) | Three branched radial (St: 25%, diblock: 40%, TV: 380 mPa·s) |   |   |   |   |
|   | (A3-5) | Three branched radial (St: 19%, diblock: 30%, TV: 550 mPa·s) |   |   |   |   |
|   |   | Total weight of (A) | 28 | 27 | 28 | 27 |
| (B) | (B1) | Tackifier resin (hydrogenated) | 57 |   | 55 | 42 |
|   | (B2) | Tackifier resin (hydrogenated) |   |   |   | 15 |
|   | (B3) | Tackifier resin (hydrogenated) |   | 46 |   |   |
|   | (B4) | Tackifier resin (hydrogenated) |   |   |   |   |
|   | (B5) | Tackifier resin (unhydrogenated) |   | 10 |   |   |
|   | (B6) | Tackifier resin (liquid) |   |   |   |   |
|   | (B7) | Tackifier resin (hydrogenated) |   |   |   |   |
| (C) | (C1) | Paraffin oil | 15 |   |   | 11 |
|   | (C2) | Paraffin oil |   | 17 | 17 |   |
|   | (C3) | Naphthene oil |   |   |   | 5 |
| (D) | (D1) | Wax |   |   |   |   |
|   |   | Total weight of (A) to (D) | 100 | 100 | 100 | 100 |
| (E) | (E1) | Antioxidant | 0.2 | 0.2 | 0.2 | 0.2 |
|   | (E2) | Antioxidant | 0.3 | 0.3 | 0.3 | 0.3 |
|   | (E3) | Antioxidant | 0.2 | 0.2 | 0.2 | 0.2 |

TABLE 2

|   |   |   | Example 5 | Example 6 | Example 7 |
|---|---|---|---|---|---|
| (A) | (A1-1) | Three branched radial (St: 39%, diblock: 80%, TV: 165 mPa·s) | 13 | 12 | 15 |
|   | (A1-2) | Three branched radial (St: 38%, diblock: 80%, TV: 184 mPa·s) |   |   |   |
|   | (A1-3) | Four branched radial (St: 38%, diblock: 80%, TV: 155 mPa·s) |   |   |   |
|   | (A1-4) | Three branched radial (St: 38%, diblock: 60%, TV: 177 mPa·s) |   |   |   |
|   | (A2-1) | Linear (St: 30%, diblock: 50%, TV: 3100 mPa·s) | 7 |   |   |
|   | (A2-2) | Linear (St: 43%, diblock: 60%, TV: 170 mPa·s) |   | 15 |   |
|   | (A2-3) | Linear (St: 16%, diblock: 56%, TV: 810 mPa·s) |   |   | 10 |
|   | (A3-1) | Three branched radial (St: 35%, diblock: 40%, TV: 490 mPa·s) |   |   |   |
|   | (A3-2) | Four branched radial (St: 40%, diblock 20%, TV; 400 mPa·s) |   |   |   |
|   | (A3-3) | 14.2 Branched radial (St: 30%, diblock: 50%, TV: 600 mPa·s) |   |   |   |
|   | (A3-4) | Three branched radial (St: 25%, diblock: 40%, TV: 380 mPa·s) |   |   |   |
|   | (A3-5) | Three branched radial (St: 19%, diblock: 30%, TV: 550 mPa·s) |   |   |   |
|   |   | Total weight of (A) | 20 | 27 | 25 |
| (B) | (B1) | Tackifier resin (hydrogenated) | 45 | 57 | 57 |
|   | (B2) | Tackifier resin (hydrogenated) |   |   |   |
|   | (B3) | Tackifier resin (hydrogenated) |   |   |   |
|   | (B4) | Tackifier resin (hydrogenated) | 15 |   |   |
|   | (B5) | Tackifier resin (unhydrogenated) |   |   |   |
|   | (B6) | Tackifier resin (liquid) |   |   |   |
|   | (B7) | Tackifier resin (hydrogenated) |   |   |   |
| (C) | (C1) | Paraffin oil | 20 | 16 | 17 |
|   | (C2) | Paraffin oil |   |   |   |
|   | (C3) | Naphthene oil |   |   |   |
| (D) | (D1) | Wax |   |   | 1 |
|   |   | Total weight of (A) to (D) | 100 | 100 | 100 |
| (E) | (E1) | Antioxidant | 0.2 | 0.2 | 0.2 |
|   | (E2) | Antioxidant | 0.3 | 0.3 | 0.3 |
|   | (E3) | Antioxidant | 0.2 | 0.2 | 0.2 |

TABLE 3

|   |   |   | Comp. Example 1 | Comp. Example 2 | Comp. Example 3 | Comp. Example 4 |
|---|---|---|---|---|---|---|
| (A) | (A1-1) | Three branched radial (St: 39%, diblock: 80%, TV: 165 mPa·s) | | | | |
|  | (A1-2) | Three branched radial (St: 38%, diblock: 80%, TV: 184 mPa·s) | | | | |
|  | (A1-3) | Four branched radial (St: 38%, diblock: 80%, TV: 155 mPa·s) | | | | |
|  | (A1-4) | Three branched radial (St: 38%, diblock: 60%, TV: 177 mPa·s) | | | | |
|  | (A2-1) | Linear (St: 30%, diblock: 50%, TV: 3100 mPa·s) | | | | |
|  | (A2-2) | Linear (St: 43%, diblock: 60%, TV: 170 mPa·s) | 23 | 25 | | |
|  | (A2-3) | Linear (St: 16%, diblock: 56%, TV: 810 mPa·s) | | | | |
|  | (A3-1) | Three branched radial (St: 35%, diblock: 40%, TV: 490 mPa·s) | | | 30 | 20 |
|  | (A3-2) | Four branched radial (St: 40%, diblock 20%, TV; 400 mPa·s) | | | | |
|  | (A3-3) | 14.2 Branched radial (St: 30%, diblock: 50%, TV: 600 mPa·s) | | | | |
|  | (A3-4) | Three branched radial (St: 25%, diblock: 40%, TV: 380 mPa·s) | | | | 10 |
|  | (A3-5) | Three branched radial (St: 19%, diblock: 30%, TV: 550 mPa·s) | | | | |
|  |  | Total weight of (A) | 23 | 25 | 30 | 30 |
| (B) | (B1) | Tackifier resin (hydrogenated) | 59 | 50 | | |
|  | (B2) | Tackifier resin (hydrogenated) | | | 50 | 50 |
|  | (B3) | Tackifier resin (hydrogenated) | | | | |
|  | (B4) | Tackifier resin (hydrogenated) | | | | |
|  | (B5) | Tackifier resin (unhydrogenated) | | | | |
|  | (B6) | Tackifier resin (liquid) | | 20 | | |
|  | (B7) | Tackifier resin (hydrogenated) | | | | |
| (C) | (C1) | Paraffin oil | 18 | 5 | | |
|  | (C2) | Paraffin oil | | | | |
|  | (C3) | Naphthene oil | | | 20 | 20 |
| (D) | (D1) | Wax | | | | |
|  |  | Total weight of (A) to (D) | 100 | 100 | 100 | 100 |
| (E) | (E1) | Antioxidant | 0.2 | 0.2 | 0.2 | 0.2 |
|  | (E2) | Antioxidant | 0.3 | 0.3 | 0.3 | 0.3 |
|  | (E3) | Antioxidant | 0.2 | 0.2 | 0.2 | 0.2 |

TABLE 4

|   |   |   | Comp. Example 5 | Comp. Example 6 |
|---|---|---|---|---|
| (A) | (A1-1) | Three branched radial (St: 39%, diblock: 80%, TV: 165 mPa·s) | | |
|  | (A1-2) | Three branched radial (St: 38%, diblock: 80%, TV: 184 mPa·s) | | |
|  | (A1-3) | Four branched radial (St: 38%, diblock: 80%, TV: 155 mPa·s) | | |
|  | (A1-4) | Three branched radial (St: 38%, diblock: 60%, TV: 177 mPa·s) | | |
|  | (A2-1) | Linear (St: 30%, diblock: 50%, TV: 3100 mPa·s) | | |
|  | (A2-2) | Linear (St: 43%, diblock: 60%, TV: 170 mPa·s) | | |
|  | (A2-3) | Linear (St: 16%, diblock: 56%, TV: 810 mPa·s) | | |
|  | (A3-1) | Three branched radial (St: 35%, diblock: 40%, TV: 490 mPa·s) | | |
|  | (A3-2) | Four branched radial (St: 40%, diblock 20%, TV; 400 mPa·s) | 15 | |
|  | (A3-3) | 14.2 Branched radial (St: 30%, diblock: 50%, TV: 600 mPa·s) | | 18 |
|  | (A3-4) | Three branched radial (St: 25%, diblock: 40%, TV: 380 mPa·s) | | |
|  | (A3-5) | Three branched radial (St: 19%, diblock: 30%, TV: 550 mPa·s) | 11 | |
|  |  | Total weight of (A) | 26 | 18 |
| (B) | (B1) | Tackifier resin (hydrogenated) | | 54 |
|  | (B2) | Tackifier resin (hydrogenated) | 53 | |
|  | (B3) | Tackifier resin (hydrogenated) | | |
|  | (B4) | Tackifier resin (hydrogenated) | | |
|  | (B5) | Tackifier resin (unhydrogenated) | | |
|  | (B6) | Tackifier resin (liquid) | | |
|  | (B7) | Tackifier resin (hydrogenated) | | 10 |
| (C) | (C1) | Paraffin oil | | |
|  | (C2) | Paraffin oil | 21 | 18 |
|  | (C3) | Naphthene oil | | |
| (D) | (D1) | Wax | | |
|  |  | Total weight of (A) to (D) | 100 | 100 |
| (E) | (E1) | Antioxidant | 0.2 | 0.2 |
|  | (E2) | Antioxidant | 0.3 | 0.3 |
|  | (E3) | Antioxidant | 0.2 | 0.2 |

With respect to the thus obtained hot-melt adhesive agents of Example and Comparative Examples, properties of a melt viscosity, a softening point, a peel strength, a retention force, loop tack were examined. The results are shown in Tables 5 and 6. The above properties were investigated by the following methods.

[Melt Viscosity]

A hot-melt adhesive agent was melted by heating at 120° C. and 140° C., and then a viscosity in a molten state was measured using a Brookfield RVT type viscometer (spindle No. 27). Evaluation criteria are as follows.

| | |
|---|---|
| ⊚ | Viscosity at 120° C. is 2,000 mPa·s to 8,000 mPa·s |
| ○ | Viscosity at 120° C. is more than 8,000 mPa·s and not more than 10,000 mPa·s |
| X | Viscosity at 120° C. is more than 10,000 mPa·s |
| ⊚ | Viscosity at 140° C. is 500 mPa·s to 3,000 mPa·s |
| ○ | Viscosity at 140° C. is more than 3,000 mPa·s and not more than 5,000 mPa·s |
| X | Viscosity at 140° C. is more than 5,000 mPa·s |

[Softening Point]

A softening point of a hot-melt adhesive agent was measured with the Ring & Ball method (the method determined as Japan Adhesive Industry Association Standard JAI-7-1999).

| | |
|---|---|
| ⊚ | Softening point is higher than 80° C. |
| ○ | Softening point is 75° C. to 80° C. |
| X | Softening point is lower than 75° C. |

[Peel Strength]

A hot-melt adhesive agent was applied to a 50 μm thick PET film in a thickness of 50 μm. The coated PET film was formed into 2.5 cm wide strips to obtain specimens. Each specimen was laid on a 100 μm thick polyethylene film at 20° C., followed by being left to stand at 20° C. for 1 day. Thereafter, peeling was performed at 10° C., 20° C. at a tension speed of 300 mm/minute and the peel strength was measured.

| | |
|---|---|
| ⊚ | Peel strength is more than 2,000 (g/25 mm) |
| ○ | Peel strength is 1,000 (g/25 mm) to 2,000 (g/25 mm) |
| X | Peel strength is less than 1,000 (g/25 mm) |

[Retention Force]

A hot-melt adhesive agent was applied to a 50 μm thick PET film in a thickness of 50 μm. The coated PET film was formed into a size measuring 2.5 cm in width to obtain specimens. A polyethylene film in a thickness of 100 μm was applied to the specimen at 20° C. so that the contact area was 1.0 cm×2.5 cm. A weight of 1 kg was hung to the polyethylene film in the direction perpendicular to the contact surface, and left under the condition of 40° C. The time elapsed before the weight of 1 kg fell was measured, and it was adopted as the retention force.

| | |
|---|---|
| ⊚ | Retention force is over 50 minutes |
| ○ | Retention force is 10 minutes to 50 minutes |
| X | Retention force is less than 10 minutes |

[Loop Tack]

A hot-melt adhesive agent was applied to a 50 μm thick PET film in a thickness of 50 μm. The coated PET film was formed into a size measuring 2.5 cm×10 cm to obtain specimens. Each specimen was wound in a loop form so that an adhesive surface (surface to be coated with an adhesive agent) faces outside, and then the loop was brought into contact with a PE sheet at 20° C. at a speed of 300 mm/minute. Then, the specimen was peeled from the PE sheet at a speed of 300 mm/minute to thereby measure the peel strength at the time of peeling, which was regarded as initial loop tack. The specimen was stored at 20° C. for a week and then brought into contact with the PE sheet at 20° C. at a speed of 300 mm/minute. Then, specimen was peeled from the PE sheet at a speed of 300 mm/minute and the peel strength at the time of peeling, which was regarded as loop tack after a week.

| | |
|---|---|
| ⊚ | Loop tack is more than 2,000 (g/25 mm) |
| ○ | Loop tack is 1,500 (g/25 mm) to 2,000 (g/25 mm) |
| X | Loop tack is less than 1,500 (g/25 mm) |

TABLE 5

| | | Example 1 | Example 2 | Example 3 | Example 4 | Example 5 | Example 6 | Example 7 |
|---|---|---|---|---|---|---|---|---|
| Viscosity (mPas) | 120° C. | 8,925 ○ | 9,400 ○ | 8,900 ○ | 8,150 ○ | 8,875 ○ | 8,100 ○ | 6,475 ⊚ |
| | 140° C. | 3,188 ○ | 2,938 ⊚ | 2,925 ⊚ | 2,925 ⊚ | 3,125 ○ | 2,975 ⊚ | 2,600 ⊚ |
| Softening point (° C.) | | 86 ⊚ | 89 ⊚ | 88 ⊚ | 84 ⊚ | 83 ⊚ | 82 ⊚ | 79 ○ |
| Peel strength (g/25 mm) | 10° C. | 2,101 ⊚ | 2,094 ⊚ | 1,978 ○ | 2,183 ⊚ | 2,178 ⊚ | 2,284 ⊚ | 2,282 ⊚ |
| | 20° C. | 1,409 ○ | 1,423 ○ | 1,191 ○ | 1,228 ○ | 1,501 ○ | 1,677 ○ | 1,700 ○ |
| Retention force (25 mm) | PET/PE | 94 ⊚ | 30 ○ | 116 ⊚ | 87 ⊚ | 14 ○ | 105 ⊚ | 14 ○ |
| | PET/PET | 97 ⊚ | 101 ⊚ | 210 ⊚ | 118 ⊚ | 39 ○ | 91 ⊚ | 14 ○ |
| Loop tack (g/25 mm) | | 2,336 ⊚ | 2,572 ⊚ | 2,525 ⊚ | 2,533 ⊚ | 2,425 ⊚ | 2,799 ⊚ | 2,581 ⊚ |

TABLE 6

|  |  | Comp. Example 1 | Comp. Example 2 | Comp. Example 3 | Comp. Example 4 | Comp. Example 5 | Comp. Example 6 |
|---|---|---|---|---|---|---|---|
| Viscosity (mPas) | 120° C. | 5,200 ◎ | 7,325 ◎ | 29,650 x | 32,400 x | 22,200 x | 11,850 x |
|  | 140° C. | 1,850 ◎ | 2,413 ◎ | 10,850 x | 11,425 x | 7,663 x | 4,088 ○ |
| Softening point (° C.) |  |  | 85 ◎ | 87 ◎ | 89 ◎ | 95 ◎ | 74 x |
| Peel strength (g/25 mm) | 10° C. | 276 x | 183 x | 1,870 ○ | 2,085 ◎ | 1,266 ○ | 38 x |
|  | 20° C. | 1,688 ○ | 1,708 ○ | 1,100 ○ | 1,095 ○ | 891 x | 674 x |
| Retention force (25 mm) | PET/PE | 23 ○ | 186 ◎ | 5 x | 7 x | 3 x | 163 ◎ |
|  | PET/PET | 70 ◎ | 300 ◎ | 1440 ◎ | 1440 ◎ | 158 ◎ | 316 ◎ |
| Loop tack (g/25 mm) |  |  | 2,631 ◎ | 1,394 ◎ | 1,435 x | 1,453 x | 789 x |

As shown in Tables 1 to 6, the hot-melt adhesive agents of Examples are excellent in melt viscosity, softening point, peel strength, retention force and loop tack since they include the component (A1). To the contrary, the hot-melt adhesive agents of Comparative Examples are significantly inferior in any one of the respective performances as compared with the hot-melt adhesive agents of Examples since they do not include the component (A1).

They were proved that, by inclusion of (A1), the hot-melt adhesive agent is improved in the above-mentioned performances, that it is able to be applied under low temperature not more than 140° C. when a disposable product is produced, and that each of parts of the disposable product hardly peels off in the winter season.

INDUSTRIAL APPLICABILITY

The present invention provides a hot-melt adhesive agent, and a disposable product which is obtained by applying the hot-melt adhesive agent. The hot-melt adhesive agent according to the present invention is particularly suitable for the production of a disposable product.

The invention claimed is:

1. A hot melt adhesive agent comprising:
(A) 3 to 60 parts by weight of a thermoplastic block copolymer consisting only of a radial styrene-conjugated diene block copolymer having (i) a styrene content of 35 to 45% by weight and a diblock content of 50 to 90% by weight (ii) a viscosity less than 250 mPa·s at 25° C. and 25% by weight in toluene solution;
(B) about 60 to about 85 parts by weight of a tackifier; and
(C) about 15 to about 20 parts by weight of an oil;
wherein the conjugated diene compound is selected from the group consisting of 1,3-butadiene, 2,3-dimethyl-1, 3-butadiene, 1,3-pentadiene, 1,3-hexadiene and combinations thereof.

2. The hot-melt adhesive agent of claim 1, wherein the radial styrene block copolymer has a structure of (S–E)$_n$Y, wherein S is a styrene block, E is a conjugated diene compound block, Y is a coupling agent and n is the number of linear block copolymers radially project from the coupling agent and has a value of 3 or 4.

3. The hot-melt adhesive agent of 1 further comprising a linear styrene block copolymer.

4. The hot melt adhesive agent of claim 1, wherein the radial styrene block copolymer is present at concentrations of 8 to 45 parts by weight.

5. The of melt adhesive agent of claim 1, wherein the radial styrene block copolymer is present at concentrations of 15 to 35 parts by weight.

6. A disposable product comprising the hot-melt adhesive agent of claim 1.

7. The disposable product of claim 6 which is a paper diaper or a napkin.

* * * * *